United States Patent
Bain (10) Patent No.: US 8,583,456 B2
(45) Date of Patent: Nov. 12, 2013

(54) SYSTEM AND METHOD FOR ADVERTISING REVENUE DISTRIBUTION

(76) Inventor: S. Clayton Bain, Phoenix, AZ (US)

( * ) Notice: Subject to any disclaimer, the term of this patent is extended or adjusted under 35 U.S.C. 154(b) by 172 days.

(21) Appl. No.: 12/985,217

(22) Filed: Jan. 5, 2011

(65) Prior Publication Data

US 2011/0166889 A1    Jul. 7, 2011

Related U.S. Application Data

(60) Provisional application No. 61/292,332, filed on Jan. 5, 2010.

(51) Int. Cl.
*G06Q 50/00* (2012.01)

(52) U.S. Cl.
USPC .............. 705/3; 705/2; 705/14.1; 705/14.4

(58) Field of Classification Search
USPC ..................... 705/2–3, 14.1, 14.4
See application file for complete search history.

(56) References Cited

U.S. PATENT DOCUMENTS

| | | | |
|---|---|---|---|
| 2005/0114883 A1* | 5/2005 | Nagai et al. | 725/34 |
| 2008/0140445 A1* | 6/2008 | Wang | 705/2 |
| 2009/0018871 A1* | 1/2009 | Essig et al. | 705/3 |
| 2009/0113008 A1* | 4/2009 | Gonzalez et al. | 709/206 |

* cited by examiner

*Primary Examiner* — Sind Phongsvirajati
(74) *Attorney, Agent, or Firm* — Snell & Wilmer L.L.P.

(57) ABSTRACT

The system monitors user actions in a user payment system and provides targeted advertisements to a user where the user opts-in as a participant in an advertising program. The system is further configured to track and distribute revenue from the advertising program to various parties including the user, healthcare providers, and user payment systems providers.

18 Claims, 4 Drawing Sheets

SYSTEM AND METHOD FOR ADVERTISING REVENUE DISTRIBUTION

CROSS REFERENCE TO RELATED APPLICATIONS

This application claims priority to U.S. Provisional Patent Application No. 61/292,332, filed Jan. 5, 2010, entitled "System and Method for Advertising Revenue Distribution," which is herein incorporated by reference in its entirety.

FIELD OF INVENTION

The present disclosure generally relates to providing incentives to users, and more particularly, to providing incentives to consumers for demonstrating desirable behaviors.

BACKGROUND OF THE INVENTION

User payment systems allow a user to access an account, via a web client, telephone system, or similar portal to view accounts, initiate payments, view actions associated with accounts, view documents associated with accounts and the like. Further, these systems acquire and include user specific information, which allows the system to characterize the preferences of a user automatically. Many of these systems are employed by healthcare providers, for example, hospitals, clinics, medical practice groups, and the like. With the rising cost of healthcare, there is a need to reduce the total cost of health services provided. Further, there is a need to provide cost effective, discounted and targeted items to a user.

SUMMARY OF THE INVENTION

Methods and systems provide users, healthcare providers, and user payment system providers with the ability to generate and allocate advertising revenue. In an embodiment, the system is configured to track a user profile and provide targeted advertising in response to the user profile, wherein the user opts into an advertising program. The system is further configured to track the revenue associated with each advertisement viewed by the user. Thereafter, the system may allocate a percentage of the revenue to various parties, such as for example, the user, healthcare providers, and user payment system providers. The user may direct this revenue to payments made through the user payment system or to an account where the revenue may accrue and earn interest.

In an embodiment, the systems and methods may be configured to receive a selection of a bill associated with user information. The user information may be collected at various times including, for example, before a visit to a healthcare provider, during a visit to a healthcare provider, and/or after a visit to a healthcare provider. The user information may also comprise one or more attributes that can be extracted from the user information. These attributes may indicate a condition or aliment. The attributes may be accessible through or extracted from an electronic medical record or other suitable medical record repository.

In an embodiment, the system and methods may be configured to select or identify advertisements based on one or more extracted attributes. The advertisements may be displayed by the systems and methods for any amount of time. Moreover, the advertisements may be selectable by a user. The advertisements may be customized to provide incentives for particular items based on the extracted attributes. The advertisements may be configured to provide one or more incentives to a beneficiary such as, for example, a medical billing system administrator, the user, and/or the healthcare provider. The attributes may be distributed to one or more beneficiary based on a set of predetermined rules, a level of use by a particular beneficiary, the amount of a bill associated with a user, or any other suitable method.

In various embodiments the systems and methods may be associated with or otherwise configured to allocate incentives to an account such that the incentives accumulate and may be applied to medical bills. In one embodiment, the systems and methods may be configured to apply the incentives to the medical bill in response to the distribution instruction, immediately without accumulating the incentives in an account. In either case, the incentives reduce the amount of the bill to be paid by the user.

BRIEF DESCRIPTION OF THE DRAWINGS

A more complete understanding of the present disclosure may be derived by referring to the detailed description and claims when considered in connection with the Figures, wherein like reference numbers refer to similar elements throughout the Figures, and:

DETAILED DESCRIPTION

The detailed description herein is presented for purposes of illustration only and not of limitation. For example, the steps recited in any of the method or process descriptions may be executed in any order and are not limited to the order presented. For the sake of brevity, conventional data networking, application development and other functional aspects of the systems (and components of the individual operating components of the systems) may not be described in detail herein.

The systems and methods include a unique combination of one or more features associated with a user payment system. In an embodiment, the user payment system may be configured with an advertising engine, such that the advertising engine may provide targeting advertisements to a user. Advertising revenue is accrued from the advertisements. The revenue may be allocated to various sources including the user, the user payment system provider, a hospital, a healthcare provider, and/or the like.

"User" may include any individual, consumer, patient, group, business, organization, government entity, benefits administrator, user payment system provider, account holder, charitable organization, software, hardware, and/or any other entity.

An "account", "account number" or "consumer account" as used herein, may include any device, code (e.g., one or more of an authorization/access code, personal identification number ("PIN"), Internet code, other identification code, and/or the like), number, letter, symbol, digital certificate, smart chip, digital signal, analog signal, biometric or other identifier/indicia suitably configured to allow the consumer to access, interact with or communicate with the system. The account number may optionally be located on or associated with a rewards account, charge account, credit account, debit account, prepaid account, telephone card, embossed card, smart card, magnetic stripe card, bar code card, transponder, radio frequency card or an associated account. The system may include or interface with any of the foregoing accounts or devices, or a transponder and RFID reader in RF communication with the transponder (which may include a fob). Typical devices may include, for example, a key ring, tag, card, cell phone, wristwatch or any such form capable of being presented for interrogation. Moreover, the system, computing unit or device discussed herein may include a "pervasive computing device," which may include a traditionally non-computerized device that is embedded with a computing unit.

A "user payment system" or "user payment account" may include any account that may be used to facilitate a financial transaction.

A "user payment system provider" or "user payment account provider" includes any entity that offers user payment account services to consumers. Although often referred to as a "financial institution," the financial institution may represent any type of bank, lender or other type of account issuing institution, such as payment services organizations. It is further noted that other participants may be involved in some phases of the transaction, such as an intermediary settlement institution.

A "financial processor," "payment network," or "payment system" or may include any software, hardware and/or entity which processes transactions, issues accounts, acquires financial information, settles accounts, conducts dispute resolution regarding accounts, and/or the like. As one of ordinary skill will recognize a financial account issuer may operate as, and provide the functions and services of a financial processor.

Phrases and terms similar to an "item" may include any good, service, information, experience, reward, points, coupons, credits, monetary equivalent, anything of value, something of minimal or no value, etc.

Figure 1:
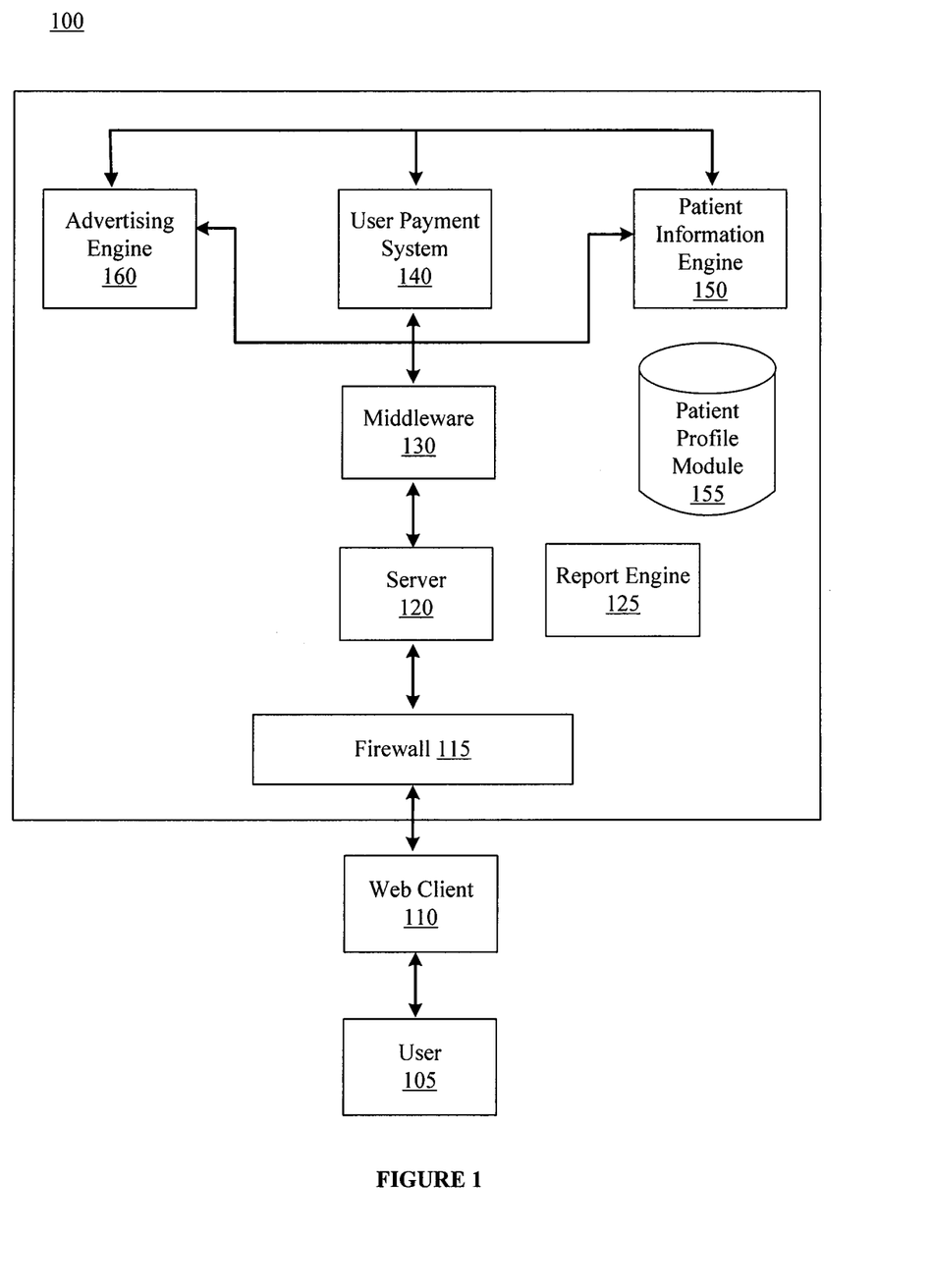
FIG. 1 is a block diagram illustrating major system components for providing advertisements to a user of a user payment system, in accordance with an exemplary embodiment of the present invention.

With reference to FIG. 1, system 100 facilitates interaction between a user 105 and a user payment account system ("UPAS") 140 through, in one embodiment, a web client 110 with a network connection to an Internet server 120 by way of the Internet. In one embodiment, Internet server 120 employs an authentication server to validate credentials, assign proper permissions, and retrieve preferences information for authorized consumers of UPAS 140. In an embodiment, Internet server 120 employs an application server to manage various applications and utilities that are utilized by system 100. In various embodiments, Internet server 120 interacts directly with the various systems and components disclosed herein. System 100 may include any number of computing platforms and databases that may be commonly found within a typical user payment system environment (e.g., at a payment processor, account issuer system, payment network, transactions database, etc.).

Such systems may include, for example, a user information engine 150, a user profile module 155, an advertising engine 160, and the like. Other systems may include, for example, new accounts systems, management information systems, business information systems, third-party data providers and the like. Each of the systems may be interconnected within by a network in via any method and/or device described herein.

A middleware server and/or application 130 may serve as an intermediary between the various systems to ensure appropriate communications between disparate platforms. A report engine 125 retrieves and/or is provided with data from the various systems in order to generate billing statements, reports, and the like.

UPAS 140 or any other components discussed herein may further include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases.

As will be appreciated by one of ordinary skill in the art, one or more of the components of system 100 may be embodied as a customization of an existing system, an add-on product, upgraded software, a stand alone system (e.g., kiosk), a distributed system, a method, a data processing system, a device for data processing, a computer and/or a computer program product. Accordingly, individual system 100 components may take the form of an entirely software embodiment, an entirely hardware embodiment, or an embodiment combining aspects of both software and hardware. In one embodiment, a system 100 component (e.g. a computer) may include a processor, a memory, a communications interface, a network interface, etc. Furthermore, individual system 100 components may take the form of a computer program product on a computer-readable storage medium having computer-readable program code means embodied in the storage medium. Any suitable computer-readable storage medium may be utilized, including hard disks, CD-ROM, flash memory, optical storage devices, magnetic storage devices, and/or the like. In one embodiment, a system 100 component and/or subsystem comprises a network interface communicating with a memory, the memory communicating with a processor; and the processor, when executing a computer program, configured to accomplish a variety of functions and/or steps.

The system contemplates uses in association with web services, utility computing, pervasive and individualized computing, security and identity solutions, autonomic computing, commodity computing, mobility and wireless solutions, open source, biometrics, grid computing and/or mesh computing.

User 105 may include any entity that utilizes system 100. User 105 may also include any entity that has a user payment account with a user payment account provider. User 105 may include a consumer who uses an account code without any physical card, uses a transponder, and/or uses a physical transaction card, to purchase items which are billed on the billing statement discussed herein. User 105 may also select payment terms relating to a revolving line of credit account, submit payments, and/or view billing statements. User 105 may be, for example, a customer who initiates payments. In an embodiment, user 105 may be, for example, a customer who receives incentives for participating in an advertising program during payments. In one embodiment, user 105 may be a consumer service representative or the like who interacts with system 100 to provide account information and configure payment terms or terms on behalf of a user. In various embodiments, user 105 may interface with UPAS 140 via any communication protocol, device or method discussed herein or known in the art. For example, user 105 may interact with UPAS 140 by way of an Internet browser at web client 110.

Web client 110 comprises any hardware and/or software suitably configured to facilitate requesting, retrieving, updating, analyzing, entering and/or modifying data. Web client 110 includes any device (e.g., personal computer) which communicates (in any manner discussed herein) with UPAS 140 via any network discussed herein. Such browser applications comprise Internet browsing software installed within a computing unit or system to conduct online transactions and/or communications. These computing units or systems may take the form of a computer or set of computers, although other types of computing units or systems may be used, including laptops, notebooks, hand held computers, set-top boxes, workstations, computer-servers, main frame computers, mini-computers, PC servers, pervasive computers, network sets of computers, and/or the like. Practitioners will appreciate that web client 110 may or may not be in direct contact with UPAS 140. For example, web client 110 may access the services of UPAS 140 through another server, which may have a direct or indirect connection to Internet server 120.

As those skilled in the art will appreciate, web client 110 includes an operating system (e.g., Windows NT, 95/98/2000/XP/VISTA/7, OS2, UNIX, Linux, Solaris, MacOS, etc.) as well as various conventional support software and drivers typically associated with computers. Web client 110 may include any suitable personal computer, network computer, workstation, minicomputer, mainframe or the like. Web client 110 can be in a home or business environment with access to a network. In an exemplary embodiment, access is through a network or the Internet through a commercially available web-browser software package.

Web client 110 may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., Gilbert Held, Understanding Data Communications (1996), which is hereby incorporated by reference. It is noted that the network may be implemented as other types of networks, such as an interactive television (ITV) network.

Web client 110 may include any number of applications, code modules, cookies, and the like to facilitate interaction with UPAS 140 in order to, for example, make a payment, view an advertising program, view statements, view payment terms, view spend information, elect a payment term, submit/authorize a payment, and the like. In one embodiment, web client 110 may store user 105 preferences and/or any other information disclosed herein on a hard drive or any other local memory device. Accordingly, web client 110 may retrieve and store user information within a memory structure of web client 110 in the form of a browser cookie, for example. In another embodiment, web client 110 retrieves information relating to user 105 from UPAS 140 on establishing a session with Internet server 120.

Firewall 115, as used herein, may comprise any hardware and/or software suitably configured to protect UPAS 140 components from users of other networks. Firewall 115 may reside in varying configurations including stateful inspection, proxy based and packet filtering among others. Firewall 115 may be integrated as software within Internet server 120, any other UPAS 140 components or may reside within another computing device or may take the form of a standalone hardware component.

Internet server 120 may include any hardware and/or software suitably configured to facilitate communications between web client 110 and one or more UPAS 140 components. Further, Internet server 120 may be configured to transmit data to web client 110 within markup language documents. As used herein, "data" may include encompassing information such as commands, queries, files, data for storage, and/or the like in digital or any other form. Internet server 120 may operate as a single entity in a single geographic location or as separate computing components located together or in separate geographic locations.

Internet server 120 may provide a suitable web site or other Internet-based graphical user interface which is accessible by consumers. In one embodiment, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, InterBase, etc., may be used to provide an Active Data Object (ADO) compliant database management system.

Any of the communications, inputs, storage, databases or displays discussed herein may be facilitated through a web site having web pages. The term "web page" as it is used herein is not meant to limit the type of documents and applications that might be used to interact with the user. For example, a typical web site might include, in addition to standard HTML documents, various forms, Java applets, JavaScript, active server pages (ASP), common gateway interface scripts (CGI), extensible markup language (XML), dynamic HTML, cascading style sheets (CSS), helper applications, plug-ins, and/or the like. A server may include a web service that receives a request from a web server, the request including a URL (e.g. http://yahoo.com/stockquotes/ge) and an IP address (e.g. 123.4.56.789). The web server retrieves the appropriate web pages and sends the data or applications for the web pages to the IP address. Web services are applications that are capable of interacting with other applications over a communications means, such as the Internet. Web services are typically based on standards or protocols such as XML, SOAP, WSDL and UDDI. Web services methods are well known in the art, and are covered in many standard texts. See, e.g., Alex Nghiem, IT Web Services: A Roadmap for the Enterprise (2003), hereby incorporated by reference.

Middleware 130 may include any hardware and/or software suitably configured to facilitate communications and/or process transactions between disparate computing systems. Middleware components are commercially available and known in the art. Middleware 130 may be implemented through commercially available hardware and/or software, through custom hardware and/or software components, or through a combination thereof. Middleware 130 may reside in a variety of configurations and may exist as a standalone system or may be a software component residing on the Internet server 120. Middleware 130 may be configured to process transactions between the various components of UPAS 140 and any number of internal or external issuer systems 100 for the purposes disclosed herein.

In order to control access to any component of UPAS 140, Internet server 120 may invoke an authentication server (not shown) in response to user 105 submissions of authentication credentials received at Internet server 120 from web client 110. The authentication server may include any hardware and/or software suitably configured to receive authentication credentials, encrypt and decrypt credentials, authenticate credentials, and grant access rights according to privileges (e.g., pre-defined privileges) attached to the credentials. The authentication server may grant varying degrees of application and data level access to users based on information stored within a database and/or any other known memory structure.

One skilled in the art will appreciate that system 100 may employ any number of databases in any number of configurations. Further, any databases discussed herein may be any type of database, such as relational, hierarchical, graphical, object-oriented, and/or other database configurations. Common database products that may be used to implement the databases include DB2 by IBM (White Plains, N.Y.), various database products available from Oracle Corporation (Redwood Shores, Calif.), Microsoft Access or Microsoft SQL Server by Microsoft Corporation (Redmond, Wash.), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one aspect of system 100, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

In one embodiment, the ability to store a wide variety of information in different formats is facilitated by storing the information as a BLOB. Thus, any binary information can be stored in a storage space associated with a data set. As discussed above, the binary information may be stored on the financial transaction instrument or external to but affiliated with the financial transaction instrument. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data associated with system 100 by multiple and unrelated owners of the data sets. For example, a first data set which may be stored may be provided by a first party, a second data set which may be stored may be provided by an unrelated second party, and yet a third data set which may be stored, may be provided by an third party unrelated to the first and second party. Each of these three exemplary data sets may contain different information that is stored using different data storage formats and/or techniques. Further, each data set may contain subsets of data that also may be distinct from other subsets.

As stated above, in various embodiments of system 100, the data can be stored without regard to a common format. However, in one exemplary embodiment, the data set (e.g., BLOB) may be annotated in a standard manner when provided for manipulating the data onto the financial transaction instrument. The annotation may comprise a short header, trailer, or other appropriate indicator related to each data set that is configured to convey information useful in managing the various data sets. For example, the annotation may be called a "condition header", "header", "trailer", or "status", herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the issuer, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, issuer, user or the like. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer may be received by a stand-alone interaction device configured to add, delete, modify, or augment the data in accordance with the header or trailer. As such, in one embodiment, the header or trailer is not stored on the transaction device along with the associated issuer-owned data but instead the appropriate action may be taken by providing to the transaction instrument user at the stand-alone device, the appropriate option for the action to be taken. System 100 contemplates a data storage arrangement wherein the header or trailer, or header or trailer history, of the data is stored on the transaction instrument in relation to the appropriate data.

One skilled in the art will also appreciate that, for security reasons, any databases, systems, devices, servers or other components of system 100 may consist of any combination thereof at a single location or at multiple locations, wherein each database or system 100 includes any of various suitable security features, such as firewalls, access codes, encryption, decryption, compression, decompression, and/or the like.

Various databases used herein may include: client data; provider data; financial institution data; and/or like data useful in the operation of the present invention. As those skilled in the art will appreciate, user computer may include an operating system (e.g., Windows NT, 95/98/2000/XP/ VISTA/7, OS2, UNIX, Linux, Solaris, MacOS, etc.) as well as various conventional support software and drivers typically associated with computers. The computer may include any suitable personal computer, network computer, workstation, minicomputer, mainframe or the like. User computer can be in a home or business environment with access to a network. In an exemplary embodiment, access is through a network or the Internet through a commercially-available web-browser software package.

As used herein, the term "network" shall include any electronic communications means which incorporates both hardware and software components of such. Communication among the parties in accordance with the present invention may be accomplished through any suitable communication channels, such as, for example, a telephone network, an extranet, an intranet, Internet, point of interaction device (point of sale device, personal digital assistant, cellular phone, kiosk, etc.), online communications, satellite communications, off-line communications, wireless communications, transponder communications, local area network (LAN), wide area network (WAN), networked or linked devices, keyboard, mouse and/or any suitable communication or data input modality. Moreover, although the invention is frequently described herein as being implemented with TCP/IP communications protocols, the invention may also be implemented using IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, Dilip Naik, Internet Standards And Protocols (1998); Java 2 Complete, various authors, (Sybex 1999); Deborah Ray And Eric Ray, Mastering Html 4.0 (1997); and Loshin, TCP/IP Clearly Explained (1997) and David Gourley and Brian Totty, HTTP, The Definitive Guide (2002), the contents of which are hereby incorporated by reference.

The invention may be described herein in terms of functional block components, screen shots, optional selections and various processing steps. It should be appreciated that such functional blocks may be realized by any number of hardware and/or software components configured to perform the specified functions. For example, system 100 may employ various integrated circuit components, e.g., memory elements, processing elements, logic elements, look-up tables, and/or the like, which may carry out a variety of functions under the control of one or more microprocessors or other control devices. Similarly, the software elements of system 100 may be implemented with any programming or scripting language such as C, C++, Java, COBOL, assembler, PERL, Visual Basic, SQL Stored Procedures, extensible markup language (XML), with the various algorithms being implemented with any combination of data structures, objects, processes, routines or other programming elements. Further, it should be noted that system 100 may employ any number of conventional techniques for data transmission, signaling, data processing, network control, and/or the like. Still further, system 100 could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

These software elements may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, may be implemented by either special purpose hardware-based computer systems which perform the specified functions or steps, or suitable combinations of special purpose hardware and computer instructions. Further, illustrations of the process flows and the descriptions thereof may make reference to user windows, web pages, web sites, web forms, prompts, etc. Practitioners will appreciate that the illustrated steps described herein may comprise in any number of configurations including the use of windows, web pages, web forms, popup windows, prompts and/or the like. It should be further appreciated that the multiple steps as illustrated and described may be combined into single web pages and/or windows but have been expanded for the sake of simplicity. In other cases, steps illustrated and described as single process steps may be separated into multiple web pages and/or windows but have been combined for simplicity.

Practitioners will appreciate that there are a number of methods for displaying data within a browser-based document. Data may be represented as standard text or within a fixed list, scrollable list, drop-down list, editable text field, fixed text field, pop-up window, and/or the like. Likewise, there are a number of methods available for modifying data in a web page such as, for example, free text entry using a keyboard, selection of menu items, check boxes, option boxes, and/or the like.

In an embodiment and with continued reference to FIG. 1, a UPAS 140 may further comprise a user information engine 150, user profile module 155, an advertising engine 160, and the like. These engines and modules may be separately or jointly configured to acquire user information, display user information, complete user initiated administrative tasks, and provide advertisements to user 105.

User information engine 150 may be any hardware and/or software configured to acquire first user information. First user information may be acquired before a visit, after a visit, and/or during a visit to a healthcare provider. This user information can be combined to create a user profile. For example, user 105 may provide health information via an electronic scheduling service in advance of an appointment, or to the doctor during the appointment. This information may include various demographic and health information (e.g. age, sex, weight, symptoms, etc.). This information may be captured by user information engine 150 before a user (e.g., patient) sees the doctor or during the doctor visit. The patient may also have medical history information (e.g. pre-existing medical conditions such as high blood pressure, prior procedures, chronic conditions, etc.). Such information may be captured by user information engine 150 through patient electronic medical/health records, medical billings (e.g., prior billings), medical billing codes, third party databases (e.g. third party electronic medical/health records provider), and/or through various other channels, such as on-line medical messaging services. This information may be captured by user information engine 150, before, during, or after the patient receives medical care.

Figure 2:
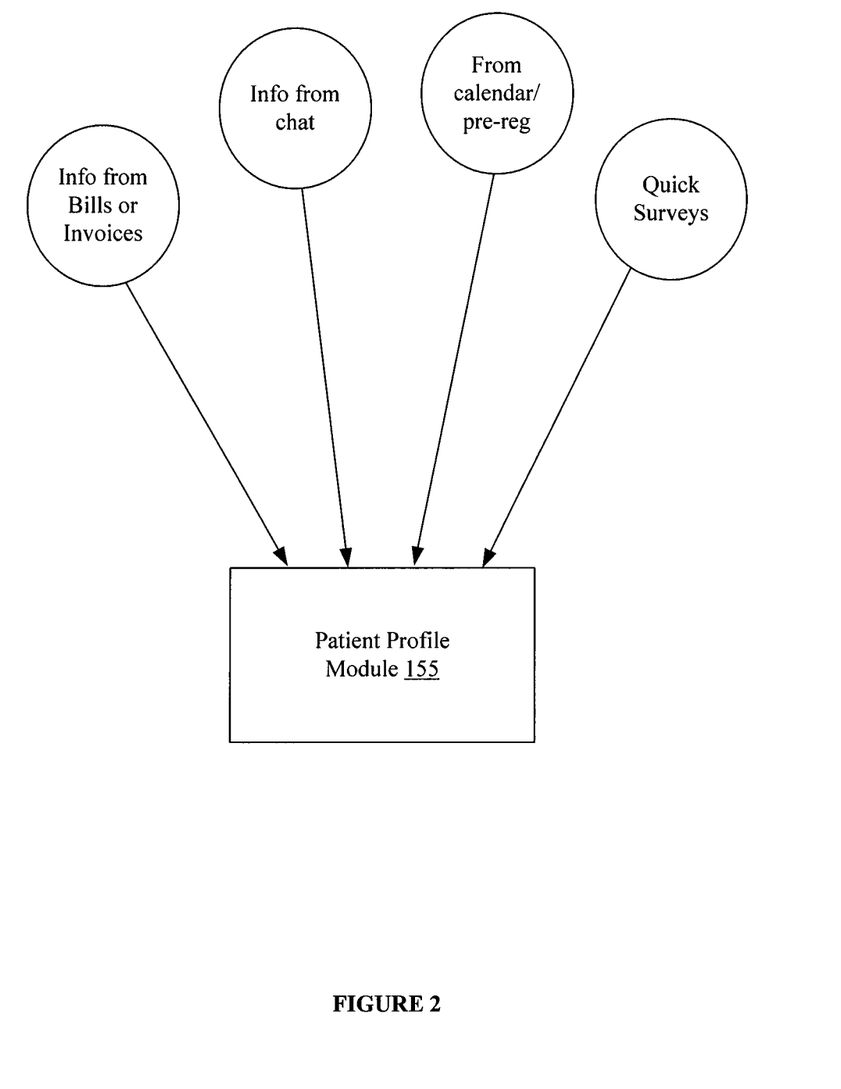
FIG. 2 is a block diagram illustrating an exemplary data source for a user profile module, in accordance with an exemplary embodiment of the present invention.

User profile module 155 may be any hardware and/or software configured to receive, combine, compile, display, transmit or create a profile for a user. User information engine 150 may provide or combine first user information with other user information, such as an existing user profile, an electronic medical/health record, or other information, as shown in FIG. 2. For example, a user that uses a UPAS 140 may have a user profile, wherein user profile module 155 collects various medical information provided by user information engine 150 to supplement the information in the user profile.

Figure 3:
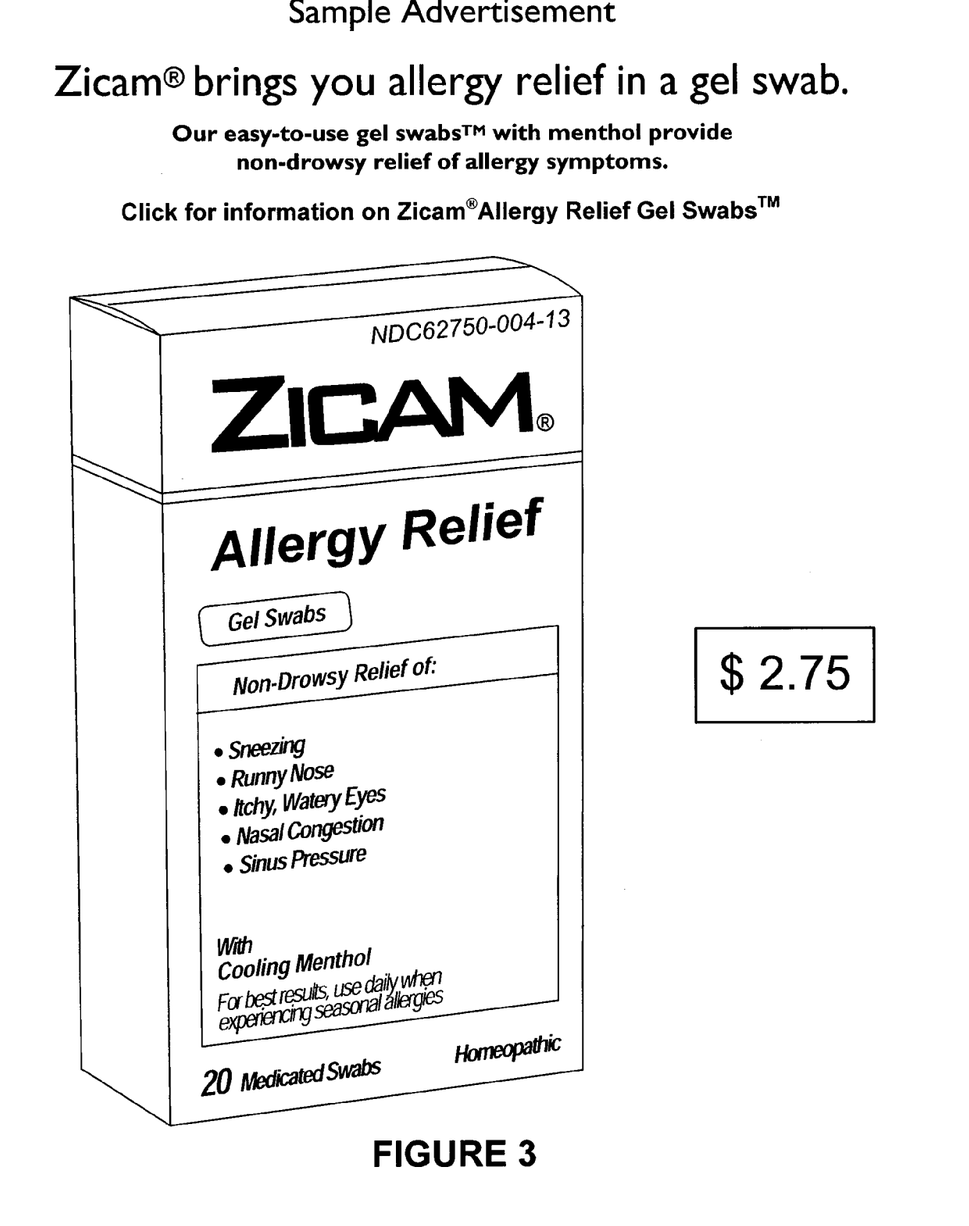
FIG. 3 is diagram illustrating an exemplary advertisement provided in accordance with an exemplary embodiment of the present invention.

Advertising engine 160 may be any hardware and/or software configured to collect and analyze user information and/or access and analyze a user profile. Advertising engine 160 may be configured to parse user data and provide targeted marketing in connection with user data. For example, in response to a user action (e.g. upon logging into a user payment system, processing a bill in a user payment system, to connecting to an on-line messenger in a user payment system, in the middle of two steps during a pre-registration or scheduling an appointment in a user payment system, etc.), advertising engine 160 is configured to display an advertisement, as shown in FIG. 3, for an item which relates to the user information provided by user information engine 150 or user profile module 155 (e.g. an advertisement for a new diabetes medication would be displayed to a diabetic user with symptoms corresponding to those the medication is intended to treat). In an embodiment, advertising engine 160 may be configured to display multiple advertisements.

Advertising engine 160 may be an advertising program within various user payment systems 140 and similar systems, including for example, bill view, payment pages, financing, point of sale software, messenger software, healthcare scheduling systems (e.g. MedPayonline's e-visit tool), pre-registration, scheduling, etc. Advertisements provided by advertising engine 160 may be directed to health, pharmaceuticals, hospital services, over the counter medicines, and various different health related services and products. Revenue may be aggregated into an account from advertising revenue and may be allocated in number of ways (the allocations do not have to be equal), including for example: 1) a portion of revenue may be allocated to provide discounts to paying users; 2) a portion of revenue may be allocated to the hospital/health care provider; 3) a portion of the revenue may be allocated to the user payment system provider.

UPAS 140 may be configured to allocate advertising revenue from ads provided by advertising engine 160. The UPAS 140 may be configured to allocate money or "credits" earned in connection with add revenue to a user's payment, balance, or account. For example, each advertisement may have a pre-determined value, such that a percentage of that value is allocated to user 105 each time the advertisement is displayed. After the advertisement is displayed, user 105 may select to apply their funds to a current payment, an outstanding balance or save them in account.

With respect to the particular method of allocating funds, any known or developed system for applying debits and credits to accounts may be used. In an embodiment, advertising revenue may used immediately or deposited in an account, such as for example a payment service account (e.g. Paypal), a traditional bank account, or in an account provided by the user payment system provider. For example, if the user decides to utilize their funds immediately, the user's funding source (e.g. a user's credit card or user's bank account) will be charged the payment due amount minus the user's share of advertising revenue. At the time of payment or potentially at the end of each business day (depending on the funding source), user payment system provider may disperse the user's share of the advertising revenue to the medical provider in the name of the user and/or patient. If the user decides to use the funds at a later date, the user payment system account may be credited with the user's portion of the advertising revenue, which may be used at any time for a medical payment through the user payment system.

Similarly, the healthcare provider's portion of the advertising revenue may be dispersed (e.g., once a day) to the healthcare provider's account, such as for example, a payment services account (e.g. Paypal), a traditional bank account, and/or the like. The healthcare provider's portion of the advertising revenue may be distributed to the provider immediately (e.g. each business day), applied to a healthcare provider account provided by a user payment account provider, and/or applied to current or future processing fees. The user payment system provider's portion of the advertising revenue may be distributed to the user payment system provider's account in any way known in the art or subsequently developed.

Figure 4:
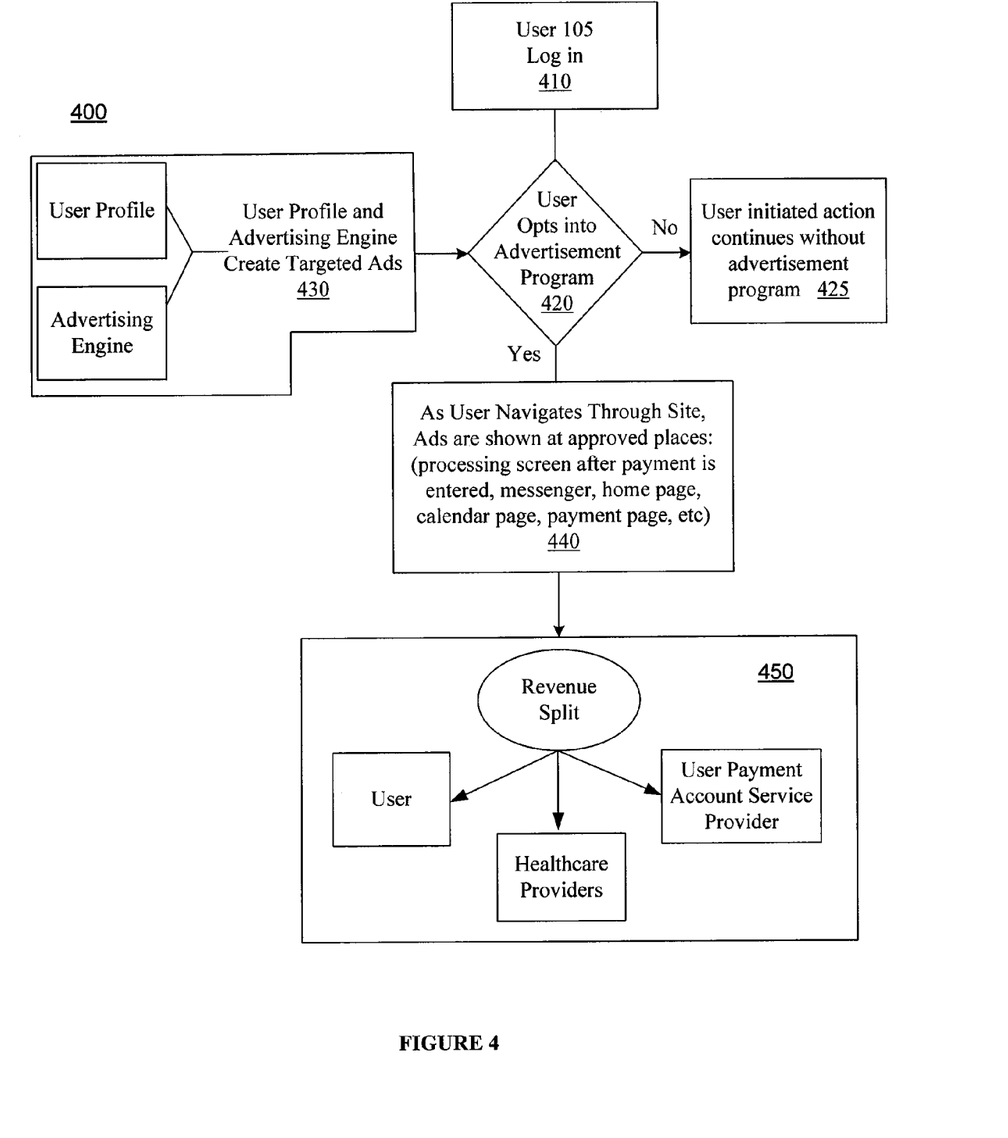
FIG. 4 is a flow chart illustrating an exemplary process displaying advertisements and allocated advertising revenue, in accordance with an exemplary embodiment of the present invention.

In summary, with respect to an exemplary method, and with reference to FIG. 4, a user payment advertising revenue distribution system is provided. User may access UPAS 140 (Step 410). Upon logging into the system, user 105 may have the option to take part in an advertising program provided via advertising engine 160 (Step 420). If user 105 chooses not to participate in the advertising program, the user initiated action continues without any action from advertising engine 160 (Step 425). If the user chooses to participate in the advertising program, advertising engine 160 may select or create advertisements based on user information, for example information from user profile, providing for targeted marketing (Step 430). As user 105 navigates through UPAS 140, advertisements are provided at specific points (e.g. setting up an account, making a payment, conversing online via messenger, or initiating another action the system) (Step 440). In response to user 105 participating in the program, a certain percentage of the revenue generated by the advertisements may be applied to a user account (Step 450). User 105 may apply all or a portion of the revenue in the account to a payment, bill, balance or maintain a balance in the account to accrue interest such that the money or credits in the account may be used for a future payment by the user. Further, advertising revenue may be allocated to a healthcare provider and/or a user payment account service provider, as shown in Step 450.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the invention. Reference to an element in the singular is not intended to mean "one and only one" unless explicitly so stated, but rather "one or more." Moreover, where a phrase similar to 'at least one of A, B, or C' is used, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. All structural, chemical, and functional equivalents to the elements of the above-described exemplary embodiments that are known to those of ordinary skill in the art are expressly incorporated herein by reference and are intended to be encompassed by the invention. Further, a list of elements does not include only those elements but may include other elements not expressly listed or inherent to such process, method, article, or apparatus.

What is claimed is:

1. A method, comprising:
   receiving, by a computer based system for administering payment of bills, a selection of a bill associated with user information;
   extracting, by the computer based system, a health related attribute from the user information;
   selecting, by the computer based system, an advertisement based on the attribute;
   determining, by the computer based system, an incentive amount in response to the selecting the advertisement, wherein the incentive amount is a monetary value and wherein monetary value is a predetermined portion of advertising revenue, and wherein the advertising revenue may be distributed among at least one of a payment system provider, a healthcare provider and a patient;
   determining, by the computer based system, a first portion of the incentive amount to be allocated to a user account based on parameters associated with the user information;
   determining, by the computer based system, a second portion of the incentive amount to be allocated to a healthcare provider, based on the first portion of the incentive amount and parameters associated with the healthcare provider;
   crediting, by the computer based system, the second portion to a healthcare provider account associated with the healthcare provider;
   receiving, by the computer based system, a distribution instruction indicating that the first portion is to be credited to the user account; and
   crediting, by the computer based system, the first portion to the user account, in response to the distribution instruction being a transfer of the first portion to the user account.

2. The method of claim 1, wherein the bill is a healthcare bill.

3. The method of claim 2, wherein the advertisement includes at least one of a product and a service associated with the health characteristic of the patient.

4. The method of claim 1, wherein the attribute is provided from an electronic medical record, and wherein the attribute is a health characteristic of a patient.

5. The method of claim 1, further comprising crediting, by the computer based system, the incentive to at least one of the user account and the healthcare provider account in response to the distribution instruction.

6. The method of claim 1, wherein the at least one of the user account and the healthcare provider account is configured to accumulate incentives that may be applied to bills.

7. The method of claim 1, further comprising crediting, by the computer based system, the incentive to the bill in response to the distribution instruction.

8. The method of claim 7, further comprising:
   reducing, by the computer based system, an amount of the bill based on the in response to the distribution instruction; and
   receiving, by the computer based system, a payment for the bill.

9. The method of claim 1, further comprising displaying, by the computer based system, the advertisement for a predetermined amount of time.

10. The method of claim 1, further comprising:
    receiving, by the computer based system, a selection of the advertisement;
    presenting, by the computer based system, an offer based on the advertisement for at least one of an item, wherein the item is associated with the attribute.

11. The method of claim 1, further comprising, receiving, by the computer based system, the distribution instruction.

12. The method of claim 1, wherein the distribution instruction is a selection made by a user.

13. The method of claim 1, wherein the distribution instruction is a predetermined action established by the user.

14. The method of claim 1, wherein the user information comprises a plurality of attributes, and wherein the attributes are compiled based on information received before a visit to a healthcare provider, during a visit to a healthcare provider, and after a visit to a healthcare provider.

15. The method of claim 1 wherein attributes are collected through at least one of an instant messenger while a user is paying the bill, payment information, eligibility information, and estimation information.

16. The method of claim 1, wherein the advertisement comprises a plurality of incentive offers.

17. A non-transitory tangible computer-readable storage medium having computer-executable instructions stored thereon that, if executed by a computer based system for administering payment of bills, causes the computer based system to perform a method comprising:
   receiving, by the computer based system, a selection of a bill associated with user information;
   extracting, by the computer based system, a health related attribute from the user information;
   selecting, by the computer based system, an advertisement based on the attribute;
   determining, by the computer based system, an incentive amount in response to the selecting the advertisement, wherein the incentive amount is a monetary value and wherein the monetary value is a predetermined portion of advertising revenue, and wherein the advertising revenue may be distributed among at least one of a payment system provider, a healthcare provider and a patient;
   determining, by the computer based system, a first portion of the incentive amount to be allocated to a user account based on parameters associated with the user information;

determining, by the computer based system, a second portion of the incentive amount to be allocated to a healthcare provider based on the first portion of the incentive amount and parameters associated with the healthcare provider;

crediting, by the computer based system, the second portion to a healthcare provider account associated with the healthcare provider;

receiving, by the computer based system, a distribution instruction indicating that the first portion is to be credited to the user account; and crediting, by the computer based system, the first portion to the user account, in response to the distribution instruction being a transfer of the first portion to the user account.

18. A system comprising:

a network interface communicating with a memory;

the memory communicating with a processor for administering payment of bills; and the processor, when executing a computer program, is configured to:

receive, by the processor, a selection of a bill associated with user information;

extract, by the processor, a health related attribute from the user information;

select, by the processor, an advertisement based on the attribute;

determine, by the processor, an incentive amount in response to the selecting the advertisement, wherein the incentive amount is a monetary value and wherein the monetary value is a predetermined portion of advertising revenue, and wherein the advertising revenue may be distributed among at least one of a payment system provider, a healthcare provider and a patient;

determine, by the processor, a first portion of the incentive amount to be allocated to a user account based on parameters associated with the user information;

determine, by the processor, a second portion of the incentive amount to be allocated to a healthcare provider based on the first portion of the incentive amount and parameters associated with the healthcare provider;

crediting, by the processor, the second portion to a healthcare provider account associated with the healthcare provider;

receive, by the processor, a distribution instruction indicating that the first portion is to be credited to the user account; and credit, by the processor, the first portion to the user account, in response to the distribution instruction being a transfer of the first portion to the user account.

\* \* \* \* \*